United States Patent
Van Brunt et al.

(10) Patent No.: US 7,018,348 B2
(45) Date of Patent: *Mar. 28, 2006

(54) METHOD AND APPARATUS FOR INDUCING SPUTUM SAMPLES FOR DIAGNOSTIC EVALUATION

(75) Inventors: Nicholas P. Van Brunt, White Bear Lake, MN (US); Donald J. Gagne, St. Paul, MN (US)

(73) Assignee: Hill-Rom Services, Inc., Wilmington, DE (US)

( * ) Notice: Subject to any disclaimer, the term of this patent is extended or adjusted under 35 U.S.C. 154(b) by 56 days.

This patent is subject to a terminal disclaimer.

(21) Appl. No.: 10/083,966

(22) Filed: Feb. 25, 2002

(65) Prior Publication Data

US 2002/0087097 A1 Jul. 4, 2002

Related U.S. Application Data (63) Continuation of application No. 09/387,312, filed on Aug. 31, 1999, now Pat. No. 6,379,316.

(51) Int. Cl.
  *A61H 23/04* (2006.01)
  *A61H 31/00* (2006.01)
(52) U.S. Cl. ............................. 601/152; 601/44
(58) Field of Classification Search ................ 600/573, 600/529, 532, 537, 538; 601/41–44, 148–152
See application file for complete search history.

(56) References Cited

U.S. PATENT DOCUMENTS

| | | | |
|---|---|---|---|
| 402,779 A | 5/1889 | Steinhoff | 601/44 |
| 2,354,397 A | 7/1944 | Miller | 601/44 |
| 2,436,853 A | 3/1948 | Coleman | |
| 2,588,192 A | 4/1952 | Akerman et al. | |
| 2,626,601 A | 1/1953 | Riley | |
| 2,762,366 A | 9/1956 | Huxley, III et al. | |
| 2,772,673 A | 12/1956 | Huxley, III | |
| 2,779,329 A | 1/1957 | Huxley, III et al. | |
| 2,780,222 A | 2/1957 | Polzin et al. | |
| 2,818,853 A | 1/1958 | Huxley, III et al. | |
| 2,832,335 A | 4/1958 | Huxley, III et al. | |
| 2,869,537 A | 1/1959 | Chu Chu | |
| 3,043,292 A | 7/1962 | Mendelson | |
| 3,063,444 A | 11/1962 | Jobst | |
| 3,120,228 A | 2/1964 | Huxley, III | |

(Continued)

FOREIGN PATENT DOCUMENTS

EP          542383 A2     5/1993

(Continued)

OTHER PUBLICATIONS

M. Tockman, et al., *The Early Detection of Second Primary Lung Cancers by Sputum Immunostaining*, Chest (Supplement), pp. 385-390, Dec. 1994.

(Continued)

*Primary Examiner*—Danton DeMille
(74) *Attorney, Agent, or Firm*—Barnes & Thornburg LLP (57) ABSTRACT

An apparatus for inducing sputum samples for diagnosing pulmonary disorders, especially as it relates to detection of early stages of lung cancer. The apparatus is comprised of a pneumatic chest compression vest, a pneumatic pressure generator, and a mouthpiece connected to a nebulizer. Sputum samples are induced by applying an oscillating force to the chest via the pneumatic chest compression vest and pressure generator, while simultaneously providing an aerosolized solution (such as normal or hypertonic saline) via the nebulizer while the patient is standing. The sample is subsequently evaluated to ascertain a patient's risk of or the presence of a pulmonary disorder such as lung cancer.

41 Claims, 5 Drawing Sheets

U.S. PATENT DOCUMENTS

| | | | |
|---|---|---|---|
| 3,191,596 A * | 6/1965 | Bird | 128/204.19 |
| 3,310,050 A | 3/1967 | Goldfarb | |
| 3,333,581 A | 8/1967 | Robinson et al. | |
| 3,454,000 A * | 7/1969 | Bird | 601/41 |
| 3,536,063 A | 10/1970 | Werding | |
| 3,566,862 A | 3/1971 | Schuh et al. | |
| 3,683,655 A | 8/1972 | White et al. | |
| 3,742,939 A | 7/1973 | Sayer | |
| 3,760,801 A | 9/1973 | Borgeas | |
| 3,802,417 A | 4/1974 | Lang | |
| 3,857,385 A | 12/1974 | Hampl | |
| 3,896,794 A | 7/1975 | McGrath | |
| 3,993,053 A | 11/1976 | Grossan | |
| 4,020,834 A | 5/1977 | Bird | 128/204.25 |
| 4,051,843 A | 10/1977 | Franetzki et al. | |
| 4,079,733 A | 3/1978 | Denton et al. | |
| 4,133,305 A | 1/1979 | Steuer | |
| 4,311,135 A | 1/1982 | Brueckner et al. | |
| 4,349,015 A | 9/1982 | Alferness | |
| 4,397,306 A | 8/1983 | Weisfeldt et al. | |
| 4,398,531 A | 8/1983 | Havstad | |
| 4,424,806 A | 1/1984 | Newman et al. | |
| 4,429,688 A | 2/1984 | Duffy | |
| 4,546,764 A | 10/1985 | Gerber | |
| 4,621,621 A | 11/1986 | Marsalis | |
| 4,676,232 A | 6/1987 | Olsson et al. | |
| 4,736,750 A | 4/1988 | Valdespino et al. | |
| 4,815,452 A | 3/1989 | Hayek | |
| 4,838,263 A | 6/1989 | Warwick et al. | |
| 4,971,042 A | 11/1990 | Lerman | |
| 4,977,889 A | 12/1990 | Budd | |
| 4,982,735 A | 1/1991 | Yagata et al. | 128/204.23 |
| 5,056,505 A | 10/1991 | Warwick et al. | |
| 5,076,259 A | 12/1991 | Hayek | |
| 5,101,808 A | 4/1992 | Kobayashi et al. | |
| 5,222,478 A | 6/1993 | Scarberry et al. | |
| 5,261,394 A | 11/1993 | Mulligan et al. | |
| 5,299,599 A | 4/1994 | Farmer et al. | 137/625.22 |
| 5,398,676 A * | 3/1995 | Press et al. | 128/204.23 |
| 5,453,081 A | 9/1995 | Hansen | 601/150 |
| 5,455,159 A | 10/1995 | Mulshine et al. | 435/7.23 |
| 5,606,754 A | 3/1997 | Hand et al. | 5/713 |
| 5,720,709 A | 2/1998 | Schnall | 600/538 |
| 5,769,797 A | 6/1998 | Van Brunt et al. | 601/41 |
| 5,806,512 A | 9/1998 | Abramov et al. | 128/204.18 |
| 5,891,062 A | 4/1999 | Schock et al. | 601/41 |
| 5,997,488 A | 12/1999 | Gelfand et al. | 601/41 |
| 6,030,353 A | 2/2000 | Van Brunt | 601/150 |
| 6,066,101 A | 5/2000 | Johnson et al. | 600/533 |
| 6,068,602 A | 5/2000 | Tham et al. | 600/533 |
| 6,155,996 A * | 12/2000 | Van Brunt et al. | 601/41 |
| 6,241,683 B1 | 6/2001 | Macklem et al. | 600/529 |

FOREIGN PATENT DOCUMENTS

| | | |
|---|---|---|
| RU | 1247009 | 1/1985 |

OTHER PUBLICATIONS

C. MacAulay, et al., *Malignancy Associated Changes in Epithelial Cells from Bronchial Biopsies*, Abstracts, Chest, p. 260.

P. Payne, et al., *Sputum Screening by Quantitative Microscopy: A Reexamination of a Portion of the National Cancer Institute Cooperative Early Lung Cancer Study*, Mayo Clinic Proceedings, vol. 72,pp. 697-704, Aug. 1997.

W. Umiker, et al., *Collection of Sputum for Cytologic Examination, Spontaneous vs. Artificially Produced Sputum*, The New England Journal of Medicine, vol. 262, pp. 565-566, Mar. 1960.

D. Rome, et al., *A Direct Comparison of Natural and Aerosol Produced Sputum Collected from 776 Asymptomatic Men*, Acta Cytologica, pp. 173-176, May-Jun. 1961.

B. Pedersen, et al., *The Value of Provoked Expectoration in Obtaining Sputum Samples for Cytologic Investigation*, Acta Cytologica, pp. 750-752, Sep.-Oct. 1985.

T. Kennedy, et al., *Efficacy of Two Sputum Collection Techniques in Patients with Air Flow Obstruction*, Acta Cytologica, pp. 630-636, Jul.-Aug. 1999.

R. Agostinis, et al., *High-Frequency Chest Compression in Combination with Hypertonic Saline Improves Sputum Cytologic Yield* (Abstract), ATS International Conference, May 1995.

M. Mckinnon, et al., *Optimal Sputum Cytology Collection Method*, Chest (Supplement), Oct. 1996.

P. Wingo, et al., *Cancer Statistics, 1995*, CA Cancer J Clin 1995, 45:8-30.

*Cancer Facts & Figures—1996*, American Cancer Society, 1996.

M. Tockman, *Survival and Mortality from Lung Cancer in a Screened Population*, The John Hopkins Study, Chest (Supplement), pp. 324-325, Apr. 1986.

R. Fontana, et al., *Lung Cancer Screening: The Mayo Program*, Journal of Occupational Medicine, vol. 28, No. 8, pp. 746-750, Aug. 1986.

*Early Lung Cancer Detection: Summary and Conclusions*, Screening for Lung Cancer, AM REV Respir dis, pp. 565-570, 1984.

L. Mao, et al., *Detection of Oncogene Mutations in Sputum Precedes Diagnosis of Lung Cancer*, Cancer Research, 54, pp. 1634-1637, Apr. 1994.

L. Mao, et al., *Microsatellite Alterations as Clonal Markers for the Detection of Human Cancer*, Proc. Natl. Acad. Sci. USA, vol. 91, pp. 9871-9875, Oct. 1994.

D. Sidransky, *Importance of Chromosome 9p Loss in Human Lung Cancer*, Journal of the National Cancer Institute, vol. 87, No. 16, Aug. 16, 1995.

M. Tockman, et al., *Sensitive and Specific Monoclonal Antibody Recognition of Human Lung Cancer Antigen on Preserved Sputum Cells: A New Approach to Early Lung Cancer Detection*, Journal of Clinical Oncology, vol. 6, No. 11, pp. 1685-1693, Nov. 1988.

R. L. Jones, et al., *Use of High Frequency Chest Compression Plus Hypertonic Saline Aerosol to Provide Sputum Samples for Diagnosis of Lung Cancer*, Abstract presented at Alberta Respiratory Diseases Symposium, Jasper, Alberta 1995.

* cited by examiner

METHOD AND APPARATUS FOR INDUCING SPUTUM SAMPLES FOR DIAGNOSTIC EVALUATION

CROSS-REFERENCE TO RELATED APPLICATION(S)

This application is a continuation of U.S. patent application Ser. No. 09/387,312, filed Aug. 31, 1999 for "Method and Apparatus for Inducing Sputum Samples for Diagnostic Evaluation" by Nicholas P. Van Brunt and Donald J. Gagne now U.S. Pat. No. 6,379,361. This application is related to U.S. patent application Ser. No. 09/387,319 for "Pneumatic Chest Compression Vest with Front Panel Bib" now abandoned and U.S. Pat. application Ser. No. 09/387,339 for "Chest Compression Vest with Connecting Belt", now U.S. Pat. No. 6,471,663 which were filed on the same day, Aug. 31, 1999, and also assigned to American Biosystems, now doing business as Advanced Respiratory.

BACKGROUND OF THE INVENTION

The present invention relates to an apparatus and method for inducing sputum samples from a patient. In particular, the present invention relates to obtaining high quality sputum samples for diagnosing pulmonary disorders, especially lung cancer.

Lung cancer has a survival rate of only 14% and is the leading cause of cancer death in the United States. The poor prognosis for lung cancer is related to both the lack of effective early detection methods, and the inability to precisely locate the diseased area of the lung to be treated. However, improved imaging techniques now allow much better tumor location capabilities, once detected, to allow specific treatment even at very early stages.

A cooperative trial undertaken by Johns Hopkins Oncology Center, Memorial Sloan-Kettering Cancer Center, and the Mayo Clinic utilized sputum induction as an early screening method to determine if a reduction in lung cancer deaths could be achieved. This study showed the resectability and survival rates among the study group were higher than among the control group, but the mortality rates were not reduced. This result led health policy groups to conclude that this type of screening method could not be justified.

These findings discouraged further research using sputum cytology for early cancer detection. Recent findings in lung tumor biology research renewed interest in the use of noninvasive techniques for screening. Biomarkers which indicate phenotypic and genotypic abnormalities and track the transformation of bronchial epithelium into a malignant tumor have been found. Sputum samples are prime candidates for diagnosing cancer with biomarkers, because it is believed that exfoliated epithelial cells recovered in sputum samples may provide the earliest indicators of lung cancer. A number of molecular genetic techniques have provided evidence that biomarkers can be detected in sputum.

Studies utilizing computer assisted, high-resolution image analysis have detected changes associated with cell transformation in normal appearing sputum samples, and also squamous cell carcinomas were detected in otherwise normal appearing epithelial cells. In addition, a number of monoclonal antibodies have been used to detect tumor-associated surface antigens on bronchial epithelial cells prior to the development of a pulmonary neoplasm. These types of studies strongly indicated that sputum cytology had the potential to improve the sensitivity, specificity, and predictive value for early diagnostic screening.

The major flaw with these methods was that repeat samplings were required to ensure adequate samples for analysis which is costly and jeopardizes a timely diagnosis. Two methods have commonly been used to collect sputum. One method uses ultrasonic nebulizer treatments to provide a mild bronchial irritant which induces a cough and supplies moisture to facilitate mucus passage. The other method is an early morning cough technique to collect samples. Four independent studies were performed which utilized the two collection methods and tried to determine whether either or both would be adequate and, therefore, useful for early diagnostic screenings. The results, however, were inconclusive.

Thus, a new method is needed to produce reliable samples while minimizing repeat sampling. This method could also be utilized to evaluate other pulmonary disorders and diseases such as asthma, chronic obstructive pulmonary disease (COPD), tuberculosis, Pneumocystis carinii pneumonia (PCP), inflammation, and infection by morphologic, immunochemical, fluorescence, molecular, or genetic techniques.

A vest apparatus has been used by clinicians to facilitate mucus passage for patients with pulmonary disorders. The most widely used device is the ABI Vest Airway Clearance System by American Biosystems, the assignee of the present application. The apparatus compresses the chest at an alternating frequency faster than breathing which increases airflow velocity, creates cough-like shear forces, decreases the viscosity of mucus, and increases mucus mobilization. This apparatus, until now, has only been used therapeutically for patients with problems such as cystic fibrosis and asthma.

BRIEF SUMMARY OF THE INVENTION

The invention discloses a method for inducing sputum from a patient, an apparatus for inducing and collecting those samples from the patient, and a method of evaluating patients for pulmonary disorders utilizing the sputum samples. The method of inducing the sputum sample includes applying an oscillating force to the chest of the patient while simultaneously providing the patient with a mouthpiece to maximize airflow velocity. In the preferred embodiment, the patient will be maintained in a standing position and also provided with a nebulizer that is connected via a port to the mouthpiece. The nebulizer produces an aerosolized solution, possibly a mild bronchial irritant, for the patient to inhale. In addition, the oscillating force is selected to maintain peak airflow velocities throughout the process.

The method of screening patients for pulmonary disorders includes collecting a sputum sample which is induced by the oscillating force and the increased airflow velocity. The sample is subsequently analyzed and the patient is assessed as to the presence of or the risk of a pulmonary disorder, for example lung cancer. The apparatus for inducing the sputum sample from a patient includes a pneumatic chest compression vest and pneumatic pressure generator to provide the oscillating force to the chest of the patient, and a mouthpiece placed in the patient's mouth. In the preferred embodiment, a source of nebulized solution is coupled to the mouthpiece, and a support is also provided to maintain the patient in a standing position. In addition, the pneumatic chest compression vest is positioned and the parameters optimized in order to maintain peak airflow velocities. Intermittently during an approximate 12 minute treatment, the treatment is stopped, and the patient expectorates the induced sputum into sampling containers.

BRIEF DESCRIPTION OF THE DRAWINGS

FIG. 3a is an illustration of a person with a mouth piece coupled to a nebulizer for providing an aerosolized solution.

FIG. 3b is a cross sectional view of the mouthpiece at line 3b—3b in FIG. 3a.

FIG. 3c is a cross sectional view of the mouthpiece at line 3c—3c in FIG. 3a.

DETAILED DESCRIPTION

Figure 1:
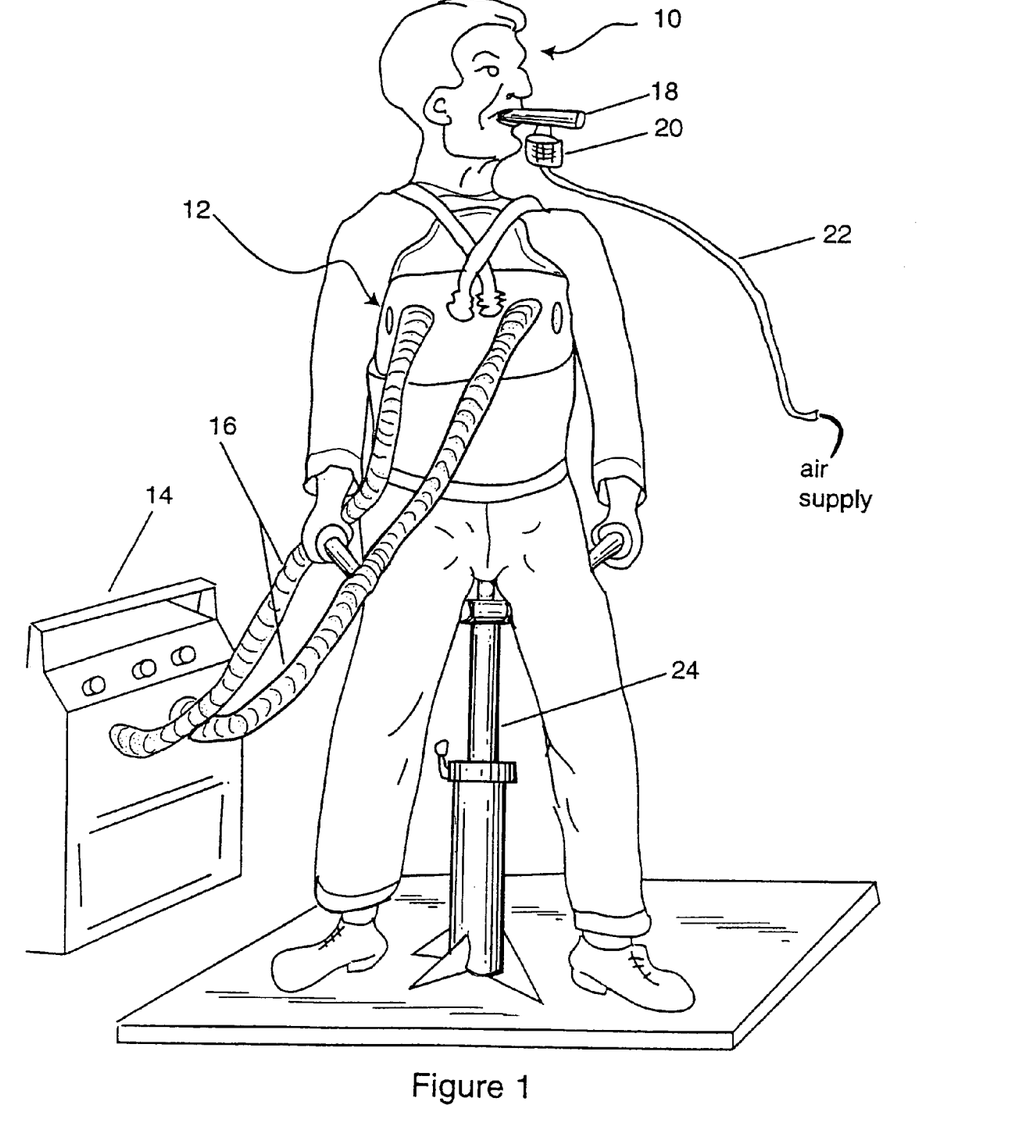
FIG. 1 is an illustration of a person using the preferred embodiment of the apparatus.
Figure 2:
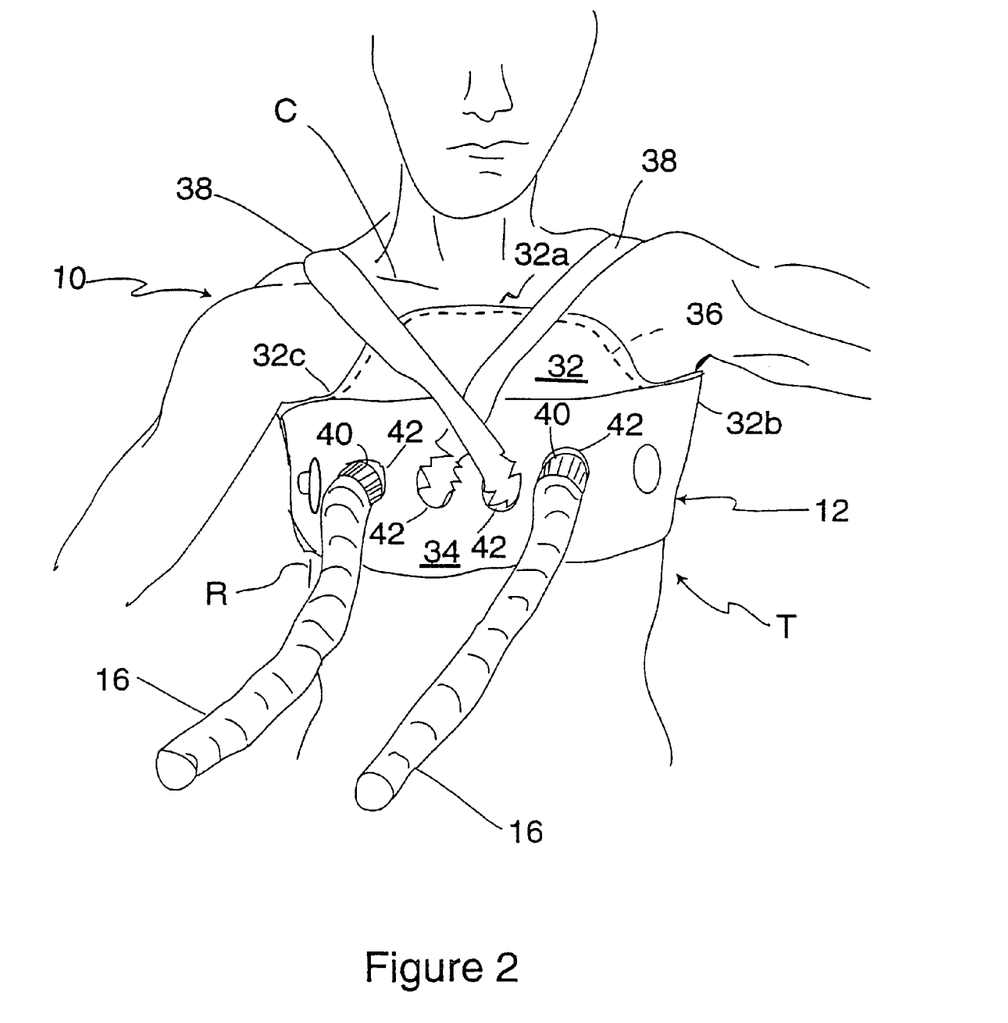
FIG. 2 is an illustration of a person fitted with a chest compression apparatus.

FIG. 1 is an illustration of person 10 undergoing treatment using the present process and apparatus. The apparatus includes pneumatic chest compression vest 12, pneumatic pressure generator 14, hoses 16, mouthpiece 18 with nebulizer 20 and air supply tube 22, and standing support 24.

Pneumatic chest compression vest 12 is worn around the upper torso of person 10. Pneumatic pressure generator 14 is connected to pneumatic chest compression vest 12 by hoses 16. Person 10 holds mouthpiece 18 in his or her mouth. Mouthpiece 18 is connected to nebulizer 20 which is supplied air by air supply tube 22 (which is connected to an air supply that is not shown). In a preferred embodiment, person 10 is kept in a standing position by standing support 24.

In operation, pneumatic pressure generator 14 maintains a positive pressure bias and delivers oscillated pneumatic pressure through hoses 16 to pneumatic chest compression vest 12, which produces oscillating chest compressions on the chest of person 10. Simultaneously, a mouthpiece is held in the mouth of person 10. In a preferred embodiment, a solution, such as a mild bronchial irritant, contained in nebulizer 20 is inhaled by person 10. Nebulizer 20 is connected to mouthpiece 18. Mouthpiece 18 maintains the airways open to maximize airflow velocities and minimizes the amount of aerosolized solution lost in the air during treatment.

The process and apparatus move the mucus, which contains exfoliated cells from the lungs, up the airway and force person 10 to cough during the treatment. The treatment is stopped, person 10 removes mouthpiece 18, coughs, and collects sputum in a cup (not shown) that is provided. Treatment is then resumed. The sputum sample is subsequently evaluated as to risk of or the presence of pulmonary disorders such as lung cancer. The combination of mouthpiece 18 with nebulizer 20 and chest compressions while in a standing position provides an optimal method for obtaining quality sputum samples.

FIG. 2 is an illustration of person 10 wearing pneumatic chest compression vest 12. This illustration demonstrates how person 10 having torso T, rib cage R, and collar bones C, is fitted into pneumatic chest compression vest 12. Pneumatic chest compression vest 12 is composed of an inelastic, flexible shell 30 (which has front panel section 32 and wrap-around belt section 34), flexible liner 36 (shown in phantom) attached to the inner surface of front panel section 32 to form a flexible air bladder, suspenders 38, and air couplings 40. A preferred embodiment of pneumatic chest compression vest 12 is described in detail in the previously mentioned related applications, which are incorporated by reference.

Front panel section 32 is shaped to cover the person's chest from the bottom of rib cage R to near collar bones C, the region of the person's chest that encompasses the lungs. Front panel section 32 has central bib portion 32A which is about 11.75 inches in height, but can range from about 9.0 inches to about 13.0 inches, and a pair of side portions 32B and 32C which are about 7.25 inches in height but can range from about 6.0 inches to about 9.0 inches. The width of front panel section 32 is about 21 inches. Side portions 32B and 32C allow front panel section 32 to extend under the person's arms. Preferably, these sections are made from 8 mil polycarbonate plastic which reduces stretching.

Flexible liner 36 covers essentially all of the inner surface of front panel section 32 and is sealed around its edges to front panel section 32. The flexible liner 36 is preferably made from 4 mil polyethylene. Together, front panel section 32 and flexible liner 36 define an air bladder which is inflated against the person's chest to apply compressive force to the chest and lungs. The compressions are focused on the region of the chest that encompasses the lungs, which effectively moves mucus from all lobes of the lungs. Air is supplied to the air bladder through a pair of ports in front panel section 32 into which air couplings 40 are inserted. Hoses 16 connect pneumatic pressure generator 14 to air couplings 40 and to the air bladder formed by front panel section 32 and flexible liner 36.

Belt section 34 is attached to side section 32B of front panel 32 and is long enough to wrap around torso T of person 10 and extend across the other side section 32C and bib section 32A. Belt section 34 has a series of longitudinally spaced belt holes 42 extending along its length. As shown in FIG. 2, two of the belt holes 42 are aligned with the ports of front panel section 32 so that air couplings 40 are inserted into belt holes 42 and into the air ports. As a result, belt section 34 is held in place around torso T and is connected to bib section 32A by air couplings 40. Other belt holes 42 on belt section 34 are used for attachment of suspenders 38.

In one embodiment, belt section 34 has a height of about 7.25 inches and a length (in the horizontal direction) of about 42 inches. Belt holes 42 are about 1.4 inches in diameter and are spaced on about 2 inch centers. Depending on the circumference of the person's chest, belt section 34 will wrap around the chest so that different belt holes 42 will be aligned with the air ports of front panel section 32. This allows pneumatic chest compression vest 12 to fit securely around person 10.

Pneumatic pressure generator 14 produces oscillatory pneumatic pressure and a positive pressure bias which is delivered through hoses 16 to the air bladder defined by front panel section 32 and liner 36. In one embodiment, the oscillatory pneumatic pressure that is delivered to the air bladder is at a frequency of between about 5 and about 25 pressure cycles per second. The oscillatory frequency preferably ranges between about 12 and about 15 pressure cycles per second, with the preferred frequency being approximately the chest resonant frequency. The force created on the chest of person 10 compresses a bronchial airway slightly. The force on the mucus (F) is related to a diameter of the airway (d) by the following equation, $F=1/d^4$. Therefore, even a slight narrowing of the airway, as caused by pneumatic chest compression vest 12, causes the force on the mucus during the outflow portion of the oscillation to increase as the fourth power of the diameter reduction. During the inflow portion of the oscillation, the airway is not compressed, and therefore, the force on the mucus is less.

This results in the mucus being pushed up and out of the airway more than it is pushed back down the airway.

The positive pressure bias that is provided to pneumatic chest compression vest 12 is about 7 inches of water (0.25 P.S.I. or 13 mm Hg). The pressure compresses the chest to create an outward airflow bias which creates the force to move the mucus. The pressure setting and frequency of force are selected for a maximum airflow velocity of greater than about 50 ml/cycle while maintaining comfort. This, in turn, maximizes the force on the mucus to increase mobilization.

Ideally, the treatment lasts for about 12 minutes but can last as long as about 20 minutes. A timer stops the treatment once it reaches about 12 minutes, but it can be restarted.

Figures 3A, 3B, 3C:
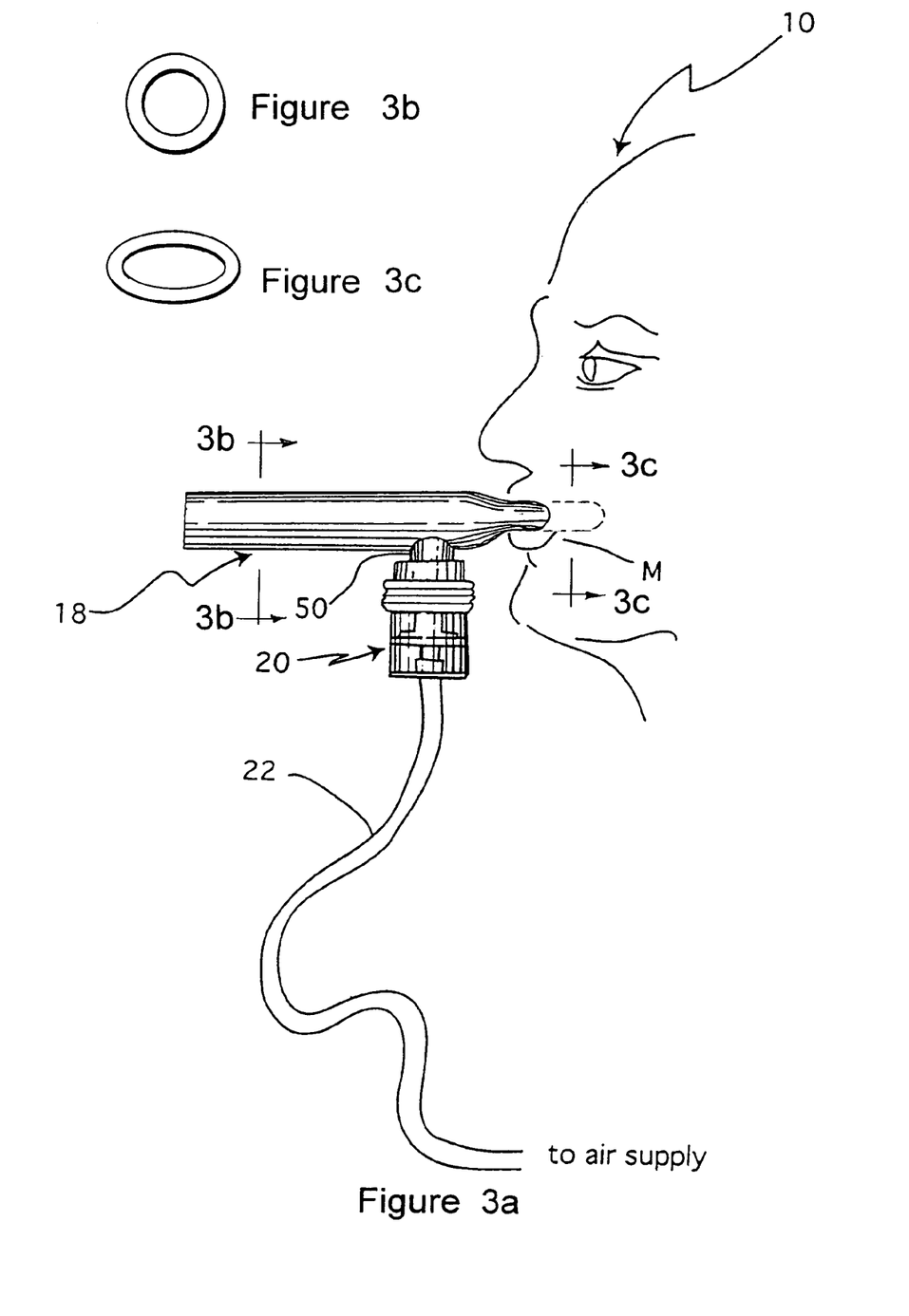

The apparatus also includes mouthpiece 18 which is illustrated in FIG. 3. This illustration demonstrates how mouthpiece 18 is used and how nebulizer 20 is connected to it. FIG. 3 shows person 10 with mouth M, mouthpiece 18, nebulizer 20, nebulizer port 50, and air supply tube 22.

The mouthpiece 18 extends into mouth M of person 10. Nebulizer 20 is coupled to mouthpiece 18 via nebulizer port 50. Nebulizer 20 is connected to an air supply via air supply tube 22.

In operation, the air supply provides a low airflow to nebulizer 20 through air supply tube 22. The airflow aerosolizes a solution, such as a mild bronchial irritant like hypertonic saline, contained in nebulizer 20 and allows person 10 to inhale the solution. The solution provides moisture to facilitate mucus mobilization, and some solutions may also help induce a cough.

Mouthpiece 18 extends about 1.5 inches into mouth M and holds open mouth M while depressing the tongue of person 10 to maximize airflow velocity. Preferably, mouthpiece 18 has an 8 inch long, 1 inch diameter extension outside mouth M beyond nebulizer 20, which limits the amount of aerosolized solution lost to the room during treatment. In a preferred embodiment, mouthpiece 18 is PVC plastic and has a generally oval cross-section and is about 1.5 inches wide by about 0.6 inches high. This size permits an airflow velocity of about 90 ml/cycle during the treatment.

Figure 4:
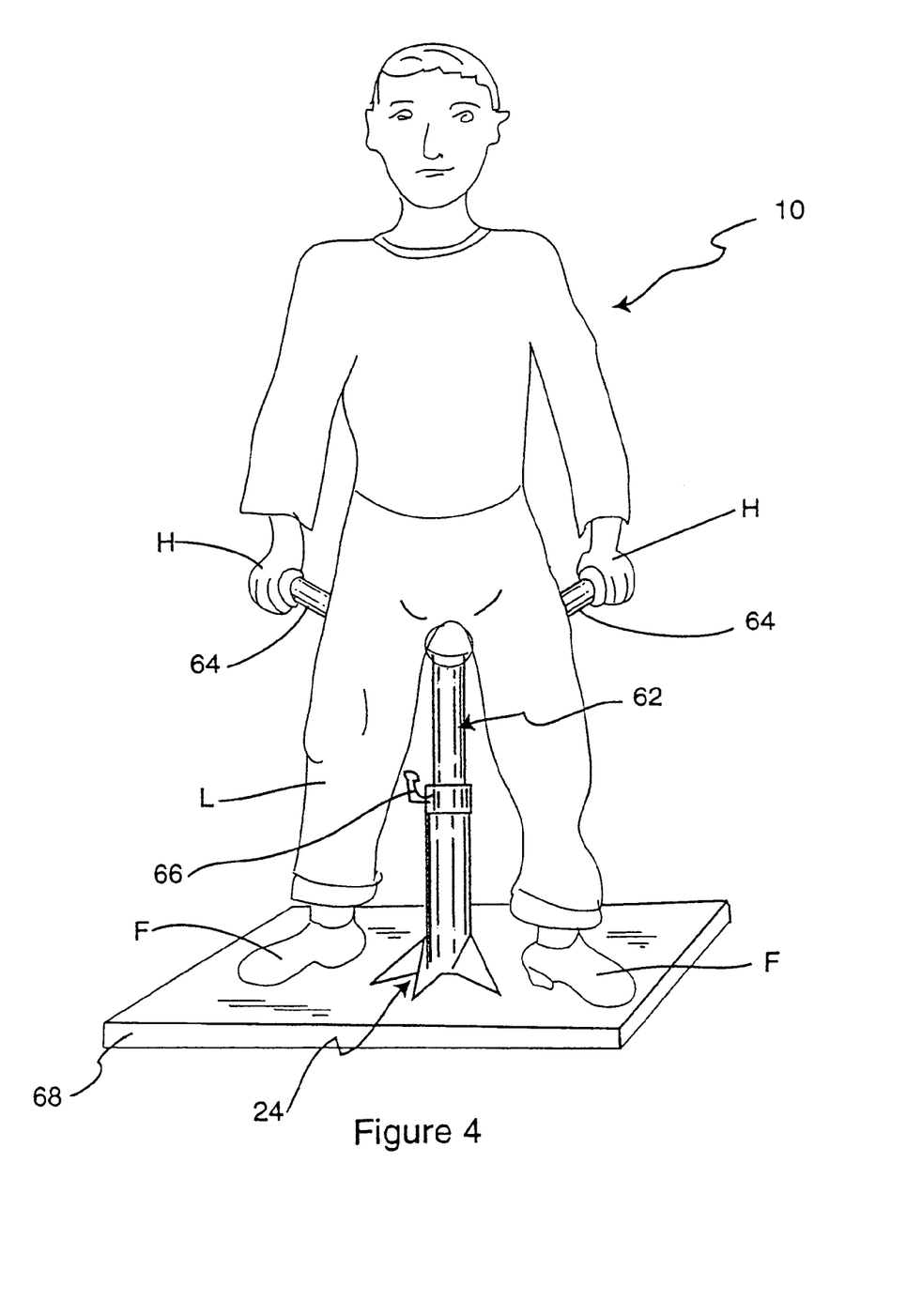
FIG. 4 is an illustration of a person and a standing support.
Figure 5:
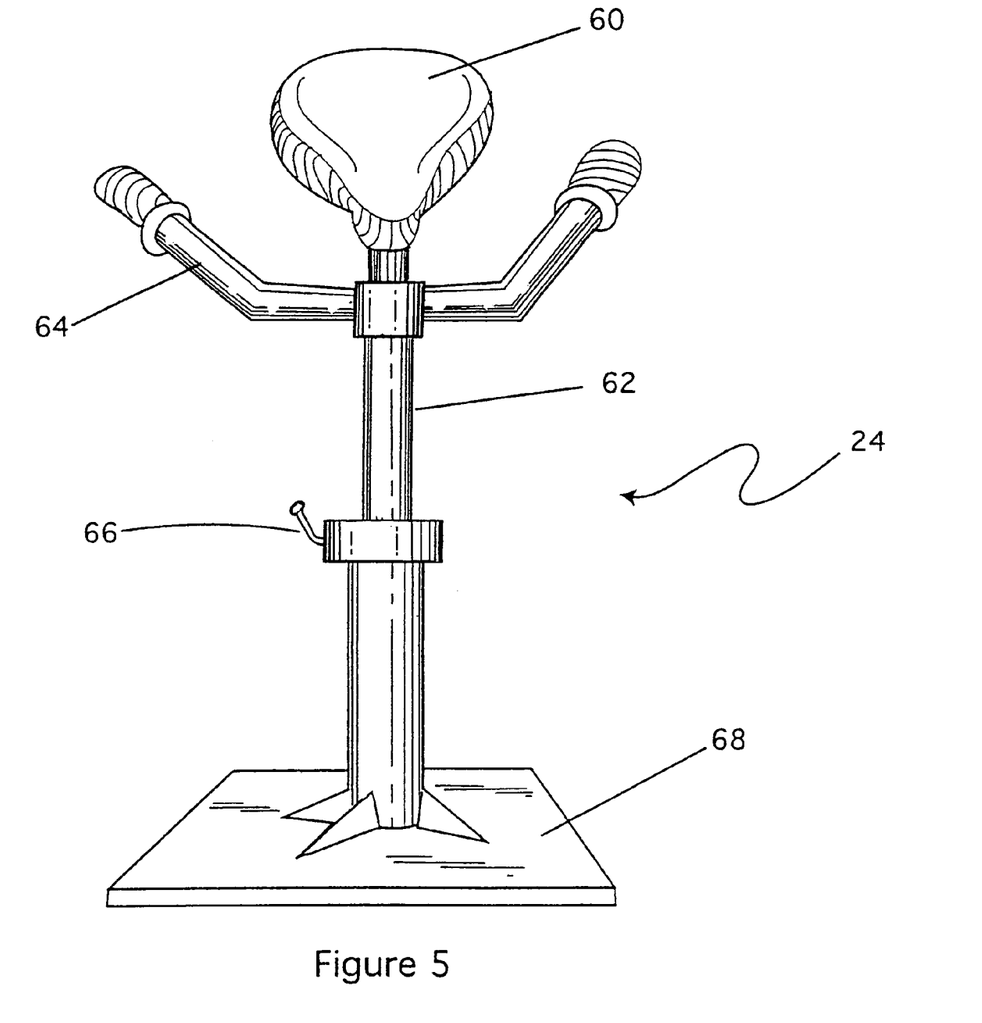
FIG. 5 is an illustration of a standing support.

In order to maximize inducement of sputum, person 10 should be kept in a standing position. FIG. 4 illustrates person 10 with feet F, legs L, and hands H using standing support 24. This figure shows how person 10 is positioned on standing support 24. As shown in FIGS. 4 and 5, standing support 24 includes seat 60, telescoping support 62, handlebars 64, height adjustment means 66, and platform 68.

Person 10 leans against seat 60. Feet F of person 10 rest on platform 68. Hands H of person 10 grip handlebars 64. Seat 60 sits on top of and is connected to support 62. Handlebars 64 are connected near the top of support 62. Support 62 rests on top of and is connected to the center of platform 68. Height adjustment means 66 is on support 62, and permits telescoping adjustment of the height of support 62 and then locks support 62 at the adjusted height. Any known height adjustment structure, such as those commonly used to adjust chair heights, can be used.

In operation, person 10 is positioned against standing support 24 as described above. Height adjustment means 66 is set so that legs L of person 10 are straight. This maintains person 10 comfortably in a standing position which is the most effective body position for the treatment, because it produces the highest airflow velocities.

Once a sputum sample has been collected using the present method and apparatus, the sample is prepared for cytological evaluation, then analyzed and assessed. In one embodiment, a sample can be assessed as to a person's risk for lung cancer.

The evaluation can also include other pulmonary disorders and diseases, such as asthma, COPD, tuberculosis, PCP, inflamation and infection, which can be diagnosed using morphologic, immunochemical, fluorescence, molecular, or genetic techniques.

Although the present invention has been described with reference to preferred embodiments, workers skilled in the art will recognize that changes may be made in form and detail without departing from the spirit and scope of the invention.

The invention claimed is:

1. An apparatus for inducing sputum from a patient, the apparatus comprising:
   a chest compression vest for applying force to a chest region of the patient;
   a pressure generator connected to the vest for providing an oscillating pressure;
   a mouthpiece having a first portion configured to extend sufficiently into the patient's mouth to depress the patient's tongue to minimize airflow resistance, the first portion of the mouthpiece placed in the patient's mouth being configured to be spaced apart from the patient's trachea, and
   a support which maintains the patient in a generally standing position.

2. An apparatus for inducing sputum from a patient, the apparatus comprising:
   a chest compression vest for applying force to a chest region of the patient;
   a pressure generator connected to the vest for providing an oscillating pressure; and
   a mouthpiece having a first portion configured to extend sufficiently into the patient's mouth to depress the patient's tongue to minimize airflow resistance, the first portion of the mouthpiece placed in the patient's mouth being configured to be spaced apart from the patient's trachea,
   wherein the pressure generator provides the oscillating pressure at at least one frequency between about 5 pressure cycles per second and about 25 pressure cycles per second.

3. The apparatus of claim 2 wherein the oscillating pressure has a frequency which is approximately a chest resonant frequency of the patient.

4. The apparatus of claim 2 wherein the oscillating pressure has a frequency between about 12 pressure cycles per second and about 15 pressure cycles per second.

5. The apparatus of claim 2 wherein the pressure generator provides a positive pressure bias to the vest.

6. The apparatus of claim 2 wherein the vest has a lower edge for positioning near a bottom of a rib cage of the patient and an upper edge for positioning near a collar bone of the patient.

7. The apparatus of claim 2 wherein the mouthpiece is removable to permit the patient to expectorate an induced sputum sample.

8. The apparatus of claim 2 wherein the first portion of the mouthpiece has a generally oval cross-section.

9. The apparatus of claim 8 wherein the first portion of the mouthpiece is about 1.5 inches wide, about 0.6 inches high and extends about 1.5 inches into the mouth.

10. The apparatus of claim 2 wherein the mouthpiece has a second portion adapted for location outside the mouth, and the second portion has a port for connection to a source of an aerosolized solution.

11. The apparatus of claim 10 wherein the second portion of the mouthpiece has a length adapted for limiting loss of the aerosolized solution.

12. The apparatus of claim 2 wherein the mouthpiece has a second portion adapted for location outside the mouth and directly communicating with atmosphere, the second portion having a length of about 8 inches.

13. The apparatus of claim 2 wherein the mouthpiece is sized to permit an airflow velocity of greater than 50 ml/cycle.

14. The apparatus of claim 13 wherein the mouthpiece is sized to permit an airflow velocity of about 90 ml/cycle.

15. The apparatus of claim 2 wherein the mouthpiece extends about 1.5 inches into the mouth.

16. The apparatus of claim 2 wherein the mouthpiece is sized to maximize airflow velocity and minimize the loss of an aerosolized solution.

17. The apparatus of claim 2 wherein a sputum sample is induced by the force applied by the chest compression vest.

18. The apparatus of claim 2, further comprising a source of an aerosolized solution coupled to the mouthpiece.

19. The apparatus of claim 18 wherein the aerosolized solution induces sputum from the patient.

20. The apparatus of claim 18 wherein a top edge of the vest is shaped to be positionable near the patient's collar bone and a bottom edge of the vest is shaped to be positionable near a bottom of the patient's rib cage.

21. An apparatus for inducing sputum from a patient, the apparatus comprising:
   means for applying force to a chest region of the patient;
   means for providing an oscillating pressure, the means for applying force being connected to the means for providing an oscillating pressure; and
   a mouthpiece having a first opening configured to be received in the patient's mouth, a second opening configured to be positioned outside the patient's mouth and communicating directly with atmosphere and a passageway extending between the first and second openings through which the patient inhales from and exhales to the atmosphere.

22. The apparatus of claim 21 and further comprising means for maintaining the patient in a generally standing position.

23. The apparatus of claim 21 wherein the means for providing an oscillating pressure provides the oscillating pressure at a frequency of between about 5 and about 25 pressure cycles per second.

24. The apparatus of claim 23 wherein the oscillating pressure has a frequency which is approximately a chest resonant frequency of the patient.

25. The apparatus of claim 23 wherein the oscillating pressure has a frequency between about 12 pressure cycles per second and about 15 pressure cycles per second.

26. The apparatus of claim 23 and further comprising means for providing a positive pressure bias to the means for applying force.

27. The apparatus of claim 21 wherein the means for applying force has a lower edge for positioning near a bottom of a rib cage of the patient and an upper edge for positioning near a collar bone of the patient.

28. The apparatus of claim 21 wherein the mouthpiece extends into the mouth, holds the mouth open and depresses a tongue of the patient.

29. The apparatus of claim 21 wherein the mouthpiece includes a first portion that extends into the patient's mouth, and the first portion has a generally oval cross-section.

30. The apparatus of claim 29 wherein the first portion is about 1.5 inches wide, about 0.6 inches high and extends about 1.5 inches into the mouth.

31. The apparatus of claim 21 wherein the mouthpiece has a second portion adapted for location outside the mouth, and the second portion has a port connected to a source of an aerosolized solution.

32. The apparatus of claim 31 wherein the second portion of the mouthpiece has a length which limits loss of the aerosolized solution.

33. The apparatus of claim 21 wherein the mouthpiece has a first portion adapted for location inside the mouth and a second portion adapted for location outside the mouth, the second portion having a length of about 8 inches.

34. The apparatus of claim 21 wherein the mouthpiece permits an airflow velocity of greater than 50 ml/cycle.

35. The apparatus of claim 34 wherein the mouthpiece permits an airflow velocity of about 90 ml/cycle.

36. The apparatus of claim 21 wherein the mouthpiece extends about 1.5 inches into the mouth.

37. The apparatus of claim 21 wherein the mouthpiece maximizes airflow velocity and minimizes the loss of an aerosolized solution.

38. The apparatus of claim 21 wherein sputum is induced by the force applied by the means for applying force.

39. The apparatus of claim 21 wherein a sputum sample is induced by the force applied by the means for applying force.

40. An apparatus for inducing sputum from a patient, the apparatus comprising:
   a chest compression vest for applying force to a chest region of the patient;
   a pressure generator connected to the vest for providing an oscillating pressure; and
   a mouthpiece having a first opening configured to be received in the patient's mouth, a second opening configured to be positioned outside the patient's mouth and communicating directly with atmosphere and a passageway extending between the first and second openings through which the patient inhales from and exhales to the atmosphere.

41. The apparatus of claim 40 wherein the mouthpiece includes a port separate from the first and second openings and communicating with the passageway, and the port is configured to be connected to a source of an aerosolized solution.

* * * * *